(12) United States Patent
Sherwood et al.

(10) Patent No.: US 8,556,894 B2
(45) Date of Patent: *Oct. 15, 2013

(54) SPHINCTEROTOME WITH STIFFENING MEMBER

(75) Inventors: Leslie P. Sherwood, Ellettsville, IN (US); Gary A. Jordan, Litchfield, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 599 days.

This patent is subject to a terminal disclaimer.

(21) Appl. No.: 12/842,339

(22) Filed: Jul. 23, 2010

(65) Prior Publication Data

US 2010/0292692 A1 Nov. 18, 2010

Related U.S. Application Data

(63) Continuation of application No. 11/557,706, filed on Nov. 8, 2006, now Pat. No. 7,766,909.

(51) Int. Cl.
*A61B 18/12* (2006.01)
(52) U.S. Cl.
USPC ............................................................ 606/47
(58) Field of Classification Search
USPC .......................................... 606/27, 34, 41, 47
See application file for complete search history.

(56) References Cited

U.S. PATENT DOCUMENTS

| 4,137,919 A | 2/1979 | Farin et al. |
|---|---|---|
| 4,325,374 A | 4/1982 | Komiya |
| 4,724,836 A | 2/1988 | Okada |
| 4,748,982 A | 6/1988 | Horzewski et al. |
| 4,762,129 A | 8/1988 | Bonzel |
| 4,905,667 A | 3/1990 | Foerster et al. |
| 4,927,418 A | 5/1990 | Dake et al. |
| 4,988,356 A | 1/1991 | Crittenden et al. |
| 5,024,617 A | 6/1991 | Karpiel |
| 5,040,548 A | 8/1991 | Yock |
| 5,061,273 A | 10/1991 | Yock |
| 5,075,062 A | 12/1991 | Karpiel |
| 5,135,535 A | 8/1992 | Kramer |
| 5,201,732 A | 4/1993 | Parins et al. |
| 5,205,822 A | 4/1993 | Johnson et al. |
| 5,232,445 A | 8/1993 | Bonzel |
| 5,279,562 A | 1/1994 | Sirhan et al. |
| 5,290,232 A | 3/1994 | Johnson et al. |
| 5,290,241 A | 3/1994 | Kraus et al. |
| 5,300,085 A | 4/1994 | Yock |
| 5,306,247 A | 4/1994 | Pfenninger |
| 5,323,768 A | 6/1994 | Saito et al. |

(Continued)

FOREIGN PATENT DOCUMENTS

| DE | 8605101 U1 | 5/1986 |
|---|---|---|
| EP | 0019930 A1 | 12/1980 |
| WO | 02/087447 A1 | 11/2002 |

*Primary Examiner* — Michael Peffley
*Assistant Examiner* — Daniel Fowler
(74) *Attorney, Agent, or Firm* — Seager, Tufte & Wickhem LLC

(57) ABSTRACT

A sphincterotome is disclosed including an elongate shaft having a lumen extending through at least a portion of the elongate shaft. The lumen includes a proximal segment and a distal segment. A cutting element extends within the lumen through the proximal segment of the lumen and extends exterior of the elongate shaft along the distal segment of the lumen. A stiffening member is positioned within the distal segment of the lumen.

17 Claims, 9 Drawing Sheets

(56) References Cited

U.S. PATENT DOCUMENTS

| | | |
|---|---|---|
| 5,324,269 A | 6/1994 | Miraki |
| 5,334,187 A | 8/1994 | Fischell et al. |
| 5,350,395 A | 9/1994 | Yock |
| 5,397,302 A | 3/1995 | Weaver et al. |
| 5,451,233 A | 9/1995 | Yock |
| 5,496,346 A | 3/1996 | Horzewski et al. |
| 5,536,248 A | 7/1996 | Weaver et al. |
| 5,547,469 A | 8/1996 | Rowland et al. |
| 5,599,299 A | 2/1997 | Weaver et al. |
| 5,599,300 A | 2/1997 | Weaver et al. |
| 5,626,600 A | 5/1997 | Horzewski et al. |
| 5,643,199 A | 7/1997 | Rowland et al. |
| 5,683,362 A | 11/1997 | Rowland et al. |
| 5,792,145 A | 8/1998 | Bates et al. |
| 5,868,698 A | 2/1999 | Rowland et al. |
| 5,968,068 A | 10/1999 | Dehdashtian et al. |
| 6,017,339 A | 1/2000 | Sadamasa |
| 6,017,340 A | 1/2000 | Cassidy et al. |
| 6,332,881 B1 | 12/2001 | Carner et al. |
| 6,443,924 B1 | 9/2002 | Rowland et al. |
| 6,547,758 B1 | 4/2003 | Rowland et al. |
| 6,579,300 B2 | 6/2003 | Griego et al. |
| 6,712,817 B1 * | 3/2004 | Goto et al. .......... 606/47 |
| 6,743,217 B2 | 6/2004 | Rowland et al. |
| 2002/0095146 A1 | 7/2002 | Hutchins et al. |
| 2002/0142119 A1 | 10/2002 | Seward et al. |
| 2003/0069575 A1 | 4/2003 | Chin et al. |
| 2004/0243056 A1 | 12/2004 | Rowland et al. |
| 2006/0074308 A1 | 4/2006 | Rafiee et al. |
| 2006/0095018 A1 | 5/2006 | Pursley |

* cited by examiner

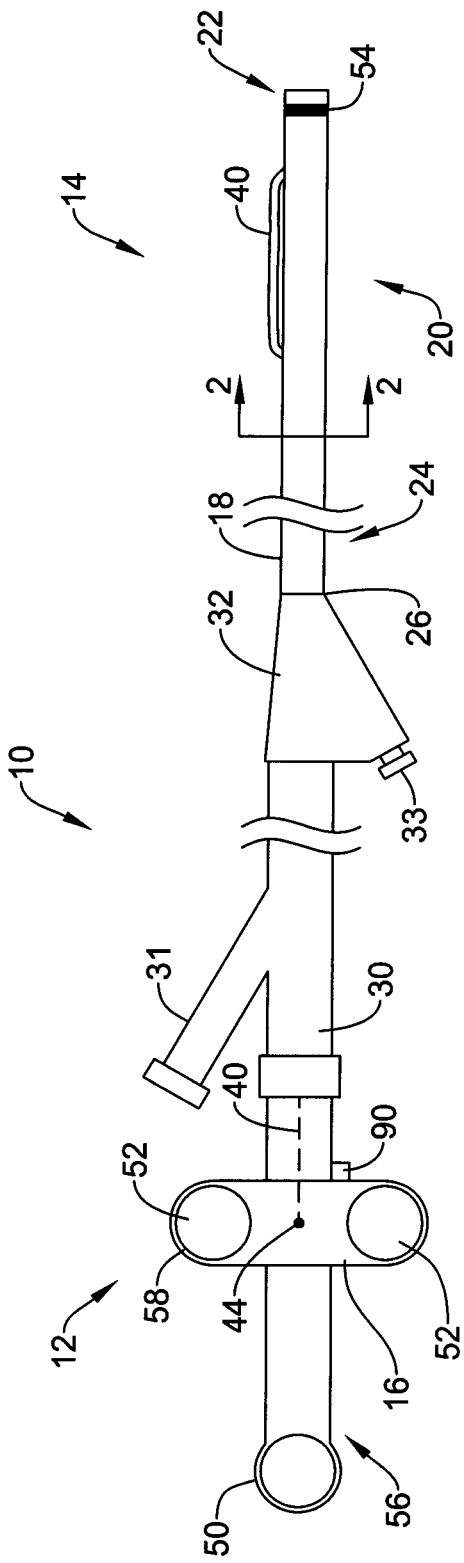
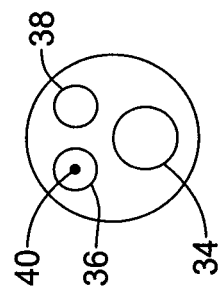
Figure 1
Figure 2

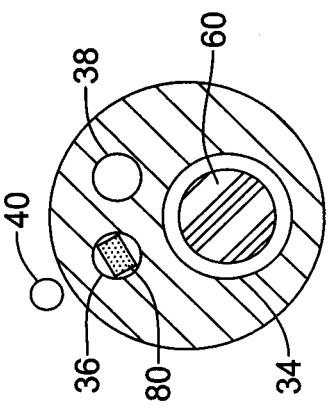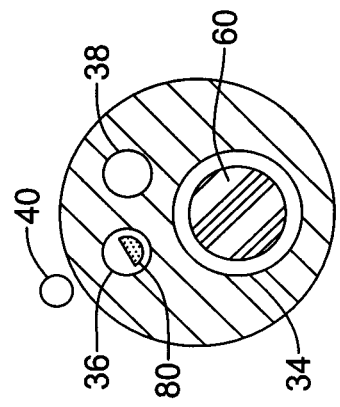

SPHINCTEROTOME WITH STIFFENING MEMBER

CROSS REFERENCE TO RELATED APPLICATIONS

This application is a continuation of co-pending U.S. application Ser. No. 11/557,706, now U.S. Pat. No. 7,766,909, filed Nov. 8, 2006, the entire disclosure of which is incorporated herein by reference.

TECHNICAL FIELD

The present invention pertains generally to medical devices and more particularly to medical devices such as sphincterotomes useful in performing diagnostic and therapeutic modalities in an anatomy, such as the biliary tree.

BACKGROUND

In medical procedures such as endoscopic sphincterotomy, a sphincterotome may be used in conjunction with an endoscope to provide surgical cutting inside of a patient. Exemplary sphincterotomes are disclosed in commonly assigned U.S. Pat. No. 6,743,217 to Rowland et al. and U.S. Pat. No. 6,579,300 to Griego et al., the disclosures of which are incorporated herein by reference. The sphincterotome may, for example, be directed through the duodenum to the sphincter of Oddi. The sphincterotome may then be used to partially incise the sphincter muscle for treatment such as removal of common bile duct stones forming an obstruction within a bile duct. A sphincterotome may include a cutting wire that can be activated by bending the sphincterotome, thereby permitting an exposed portion of the cutting wire to form a chord extending between two points along the distal portion of the sphincterotome.

However, when activating the cutting wire, it may be difficult to control the exact positioning of the cutting wire. In some instances, it may be desirable to position the activated cutting wire in an angular configuration commonly referred to in the art as the "12 o'clock" position, or in any other desirable angular configuration. Additionally, the tip portion of the sphincterotome may be prone to kinking or whipping when the cutting wire is actuated.

There remains a need, therefore, for an improved sphincterotome that is configured such that, when activated, the cutting wire assumes a desired cutting position at or near the "12 o'clock" position, or any other desired angular configuration. A need remains for an improved sphincterotome with controlled bending characteristics which improves orientation, bowing, cutting, and/or rigidity, and/or reduces kinking and/or whipping of the tip during a medical procedure.

SUMMARY

The disclosure is directed to a sphincterotome including an elongate shaft, a cutting element, and a stiffening member positioned within a lumen of the distal region of the elongate shaft.

Accordingly, one illustrative embodiment is a sphincterotome including an elongate shaft having a cutting element lumen and a guidewire lumen each extending through at least a portion of the elongate shaft. The sphincterotome also includes a cutting element, wherein a portion of the cutting element is disposed within the cutting element lumen and a portion of the cutting element lumen is disposed exterior to the cutting element lumen such that a portion of the length of the cutting element lumen is vacant of the cutting element. A stiffening member is disposed in at least a portion of the portion of the cutting element lumen vacant of the cutting element.

Another illustrative embodiment is a sphincterotome including an elongate shaft having a lumen extending through at least a portion of the elongate shaft. The elongate shaft includes a first side port providing access to the lumen, and a second side port providing access to the lumen. The second side port is located a distance from the first side port, wherein a portion of the lumen extends between the first side port and the second side port. The sphincterotome also includes a cutting element, wherein a first portion of the cutting element extends through a first segment of the lumen and a second portion of the cutting element extends between the first side port and the second side port external of the elongate shaft. A stiffening member is positioned within at least a portion of a second segment of the lumen, wherein the second segment of the lumen is defined between the first side port and the second side port.

Yet another illustrative embodiment is a sphincterotome including an elongate shaft having a cutting element lumen and a guidewire lumen each extending through at least a portion of the elongate shaft. The cutting element lumen includes a proximal segment and a distal segment. The sphincterotome also includes a cutting element extending within the cutting element lumen through the proximal segment of the cutting element lumen and extending exterior of the elongate shaft along the distal segment of the cutting element lumen. A stiffening member is positioned within at least a portion of the distal segment of the cutting element lumen.

BRIEF DESCRIPTION OF THE DRAWINGS

The invention may be more completely understood in consideration of the following detailed description of various embodiments in connection with the accompanying drawings, in which:

FIG. 1 is a plan view of an exemplary sphincterotome;

FIG. 2 is a cross-sectional view taken along line 2-2 of FIG. 1;

FIG. 4A is a cross-sectional view taken along line 4A-4A of FIG. 3;

FIGS. 4B-4D are alternative cross-sectional views of a distal section of an exemplary sphincterotome;

Figure 3:
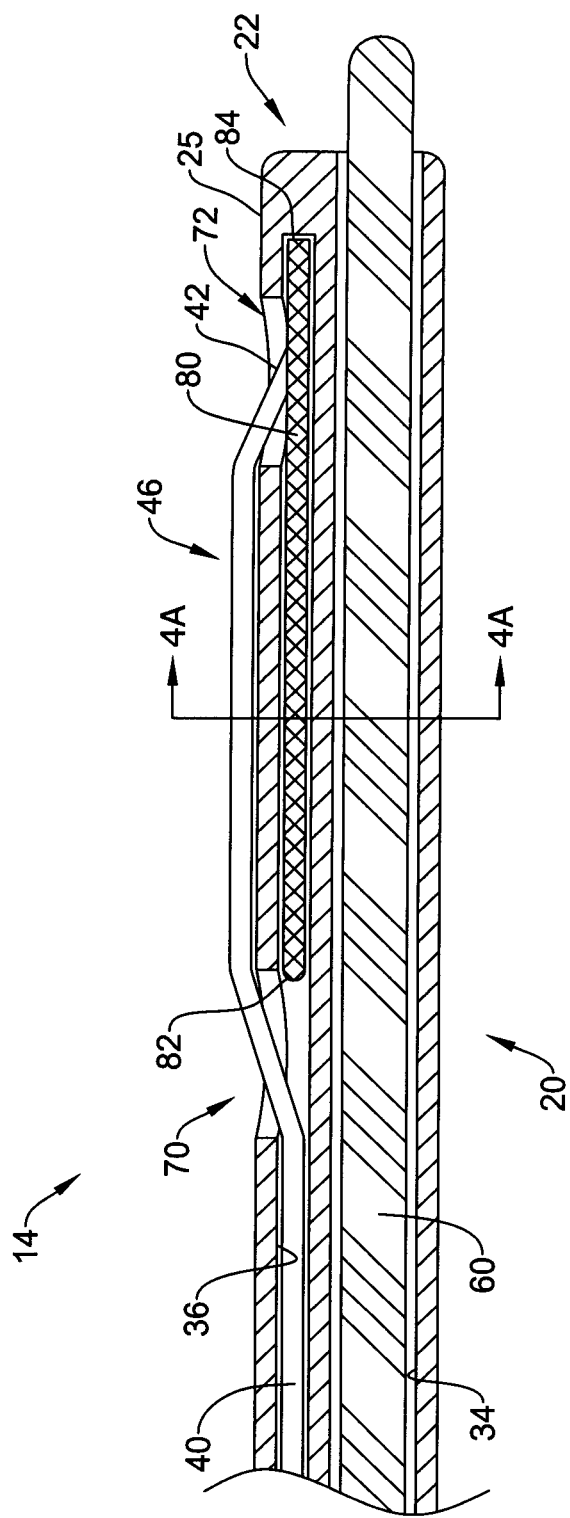
FIG. 3 is an enlarged cross-sectional view of the distal section of the exemplary sphincterotome of FIG. 1.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, a sphincterotome 10 is generally illustrated. The sphincterotome 10 can be seen as including a proximal section 12 and a distal section 14. A handle 16 is disposed within the proximal section 12 and an elongate shaft 18 extends distally therefrom. The handle 16 may be formed of any suitable material, such as a metallic or polymeric material including, but not necessarily limited to those discussed herein.

In some embodiments, the sphincterotome 10 may include one or more hubs, such as a first hub 30 and a second hub 32, disposed in the proximal section 12 of the sphincterotome 10. In some instances, if desired, the first hub 30 may include a port 31 that may be used to gain fluid access to an interior of the elongate shaft 18. Additionally, or alternatively, if present, the second hub 32 may include a port 33, such as a guidewire port, providing guidewire access to the interior of the elongate shaft 18. The hubs 30, 32 may be formed of any suitable material, such as those materials listed elsewhere herein.

The elongate shaft 18 may be formed of or include any suitable material, such as a polymeric material. Some suitable polymeric materials include, but are not necessarily limited to, polyamide, polyether block amide, polyethylene, polypropylene, polyvinylchloride, polyurethane, and copolymers, blends, mixtures or combinations thereof. In some cases, the elongate shaft 18 may include portions made from or including polytetrafluoroethylene (PTFE), commonly known as TEFLON®. The elongate shaft 18, which includes a distal region 20 and a proximal region 24, extends from a distal end 22 to a proximal end 26. The proximal end 26 may extend into, be secured to or otherwise extend distally from the handle 16, the first hub 30 and/or the second hub 32.

FIG. 2, which is a cross-section taken through the elongate shaft 18, provides an illustrative, non-limiting, example of an interior of the elongate shaft 18. As shown in FIG. 2, it can be seen that the elongate shaft 18 includes a first lumen 34, a second lumen 36 and a third lumen 38. Although three lumens are illustrated in FIG. 2, it is noted that in some embodiments, the elongate shaft 18 may include only one lumen, may include only two lumens, or may include additional lumens, as desired. In some embodiments, one or more of the lumens may extend from the proximal end 26 to the distal end 22 of the elongate shaft 18, or any portion of the length of the elongate shaft 18. For instance, the first lumen 34, which may be considered a guidewire lumen in some embodiments, may only extend through a distal portion of the elongate shaft 18. However, in other embodiments, the first lumen 34 may extend through substantially the entire length of the elongate shaft 18. Furthermore, the second lumen 36, which may be considered a cutting element lumen in some embodiments, may terminate proximal of the distal end 22 of the elongate shaft 18.

In the illustrative embodiment, the first lumen 34 may, for example, be a guidewire lumen in communication with the guidewire port 33 within the second hub 32. The second lumen 36 may, for example, accommodate or house a cutting element 40. The third lumen 38, may, for example, be a fluid delivery lumen, such as a contrast fluid lumen, in fluid communication with the port 31 of the first hub 30.

Returning to FIG. 1, the cutting element 40 may extend from the handle 16 to a position within the distal region 20 of the elongate shaft 18. The cutting element 40, for example a cutting wire as known in the art, may be a multifilament wire such as a braided wire, or a monofilament wire. The cutting wire may have a selected cross-sectional geometry including, for example, round, rectangular, triangular, or any other shape. It should be noted that the cutting element 40 has a distal end (discussed later with respect to FIGS. 3 and 5-9) and a proximal end 44. In some embodiments, the proximal end 44 of the cutting element 40 may be secured to the handle 16. More particularly, in some embodiments, the handle 16 may include a stationary portion 56 and an actuatable portion 58. The stationary portion 56 of the handle 16 may be secured to the elongate shaft 18, while the proximal end 44 of the cutting element 40 may be secured to the actuatable portion 58 of the handle 16. In some embodiments, the actuatable portion 58 may be slidably disposed on the stationary portion 56, such that the actuatable portion 58 may be slidably actuated relative to the stationary portion 56. In other embodiments, the cutting element 40 may be actuated (e.g., longitudinally translated relative to the elongate shaft 18) by other means.

The stationary portion 56 may, in some embodiments, include a thumb ring 50 while the actuatable portion 58 may include one or more finger rings 52. Thus, in such embodiments, the physician or other operator may activate the sphincterotome 10 by holding the thumb ring 50 in his/her thumb and using his/her fingers to manipulate the finger rings 52, and thus the actuatable portion 58. Manipulation of the finger rings 52 actuates the cutting element 40 proximally and/or distally (e.g., longitudinal translation) relative to the elongate shaft 18 such that an exposed portion of the cutting element 40 forms a chord between two points along the distal region 20 of the elongate shaft 18.

The handle 16 may also, in some embodiments, include a connector block 90 that may be used to provide communication between the cutting element 40 and an energizing source, such as an RF heating source, as is known in the art, in order to stimulate the cutting element 40.

The distal region 20 of the elongate shaft 18 may, as illustrated, include one or more radiopaque markers such as marker bands 54. The marker bands 54, if present, may be formed of any suitable radiopaque material and may have any appropriate dimensions and/or axial spacing, as desired. The marker bands 54 may aid in positioning the sphincterotome 10 during a medical procedure. Alternatively, the catheter may include a radiopaque filler within the materials forming at least a portion of the catheter.

FIG. 3 is an enlarged cross-sectional view of the distal section 14 of the sphincterotome 10. As shown in FIG. 3, a guidewire 60 is shown extending through the first lumen 34. The guidewire 60 may facilitate navigation and/or placement of the sphincterotome 10 within the anatomy of a patient during a medical procedure.

The distal region 20 of the elongate shaft 18 may include a first side port 70 and a second side port 72. The first side port 70 may provide access through the wall of the elongate shaft 18 to the second lumen 36. Similarly, the second side port 72 may provide access through the wall of the elongate shaft 18 to the second lumen 36. The first side port 70 may be positioned a distance proximal of the second side port 72, wherein the second lumen 36 continues between the first side port 70 and the second side port 72. In some embodiments the first side port 70 may be about 5 millimeters or more, about 10 millimeters or more, about 20 millimeters or more, or about 30 millimeters or more proximal of the second side port 72. For example, in some embodiments, the first side port 70 may be about 5, 10, 15, 20, 25, 30, 35, or 40 millimeters proximal of the second side port 72. Thus, the length of the segment of the second lumen 36 spanning the first side port 70 and the second side port 72 may have a corresponding length. Although some suitable dimensions are disclosed, one of skill in the art would understand that desired dimensions may deviate from those expressly disclosed.

The placement of the cutting element 40 may be further described while referring to FIG. 3. The cutting element 40 may extend within the second lumen 36 through a portion of the elongate shaft 18 just proximal of the first side port 70. The cutting element 40 may then exit the second lumen 36 at the first side port 70 and continue distally exterior of the elongate shaft 18, such that the second lumen 36 is vacant of the cutting element 36 through a portion of the length of the second lumen 36. The cutting element 40 may reenter the elongate shaft 18 at the second side port 72. Therefore, the portion of the cutting element 40 extending between the first side port 70 and the second side port 72 external of the second lumen 36 may constitute an exposed portion 46 of the cutting element 40.

A stiffening member 80 may be positioned within at least a portion of the length of the segment of the second lumen 36 vacant of the cutting element 40. The stiffening member 80 may have a proximal end 82 and a distal end 84. In some embodiments, the proximal end 82 of the stiffening member 80 may be proximate the first side port 70 and the distal end 84 of the stiffening member 80 may be proximate the second side port 72. In some embodiments, the stiffening member 80 may be disposed in a majority of the length of the segment of the second lumen 36 vacant of the cutting element 40. In other embodiments, the stiffening member 80 may be disposed in a substantial portion of the length of the segment of the second lumen 36 vacant of the cutting element 40. In some embodiments, the stiffening member 80 may be disposed in 25% or more, 40% or more, 50% or more, 60% or more, 75% or more, or 90% or more of the length of the segment of the second lumen 36 vacant of the cutting element 40. For example, in some embodiments, the stiffening member 80 may have a length of about 10 to about 20 millimeters and the length of the second lumen 36 vacant of the cutting element 40 may be about 20 millimeters. In other embodiments, the stiffening member 80 may have a length of about 20 to about 30 millimeters and the length of the second lumen 36 vacant of the cutting element 40 may be about 30 millimeters. Thus, in some embodiments, the stiffening member 80 may extend parallel with the exposed portion 46 of the cutting element 40 and/or the stiffening member 80 may extend along a common longitudinal length with the exposed portion 46 of the cutting element 40.

In some embodiments, the distal end 42 of the cutting element 40 may be secured to the stiffening member 80. For example, the cutting element 40 may be secured to the stiffening member 80 by welding, brazing, soldering, adhesive bonding, fusion bonding, crimping, mechanical fastening, twisting, looping, bending, or the like. Thus, in some embodiments, the stiffening member 80 may act as an anchor for the distal end 42 of the cutting element 40.

In some embodiments, the stiffening member 80 may be a solid member, as shown in FIG. 3, or, in other embodiments, the stiffening member 80 may be a tubular member or a filler of material, for example. For instance, the stiffening member 80 shown in FIG. 3 may be a solid wire. The stiffening member 80 may be formed of any suitable material. Some suitable materials include metals such as stainless steel alloys, and shape memory alloys, such as nickel-titanium alloys, some of which are commonly referred to as nitinol. Some suitable polymers include those polymers listed herein, as well as shape memory polymers. One of skill in the art would understand that other undisclosed materials may be suitable in forming the stiffening member 80.

Stiffening member 80 may be designed to adhere well with the catheter material. Alternatively, adhesives, melting or a tie layer can be used. The surface of member 80 may be etched, scraped or roughened to improve connection to the catheter. Stiffening member 80 may further include apertures, slots, bumps, dents and combinations thereof to aid attachment and control flexibility of the stiffening member 80.

Figure 3A:
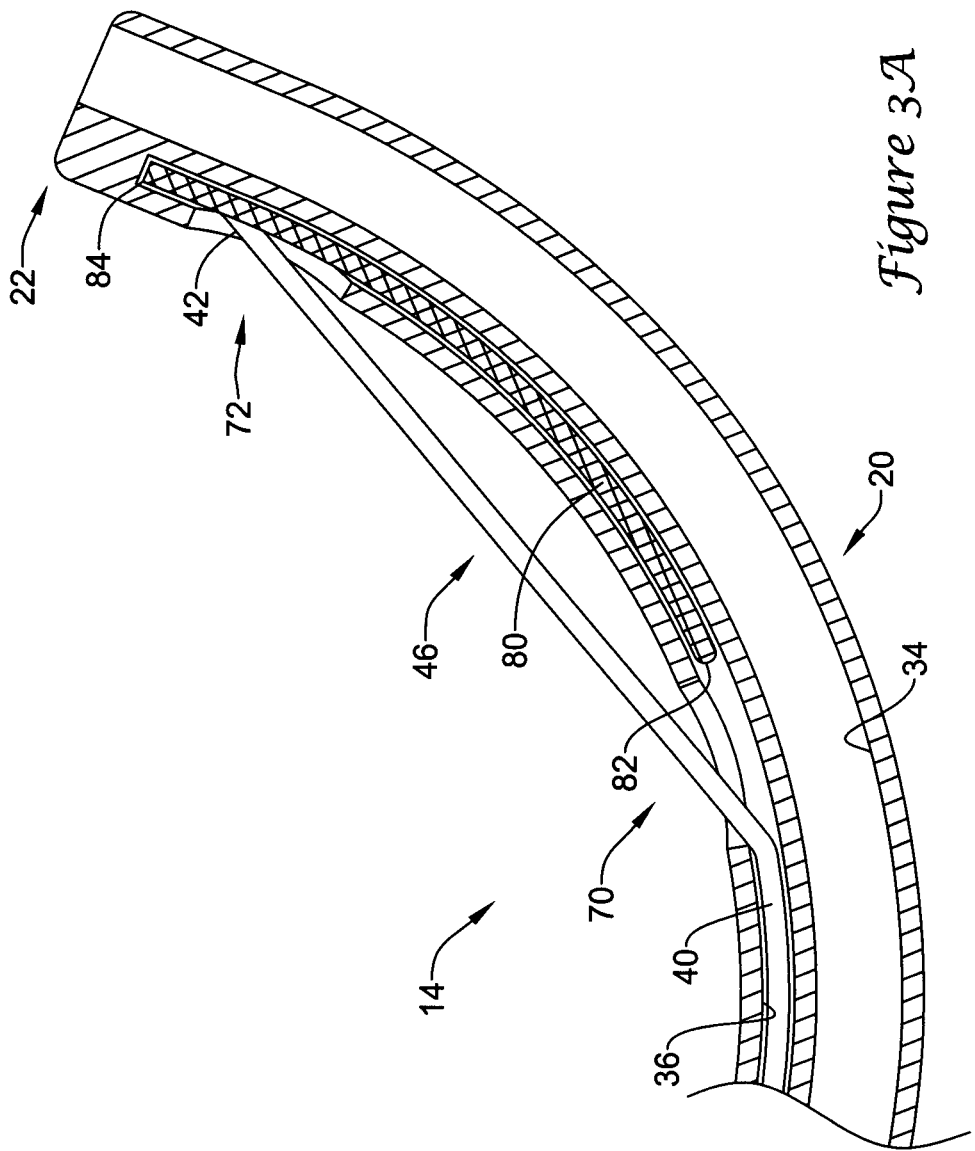
FIG. 3A is an enlarged cross-sectional view of the distal section of the exemplary sphincterotome of FIG. 1 in an activated, bowed configuration.

The exposed portion 46 of the cutting element 40 and/or the stiffening member 80 may be subjected to a cold-forming process to provide desired characteristics to the cutting element 40 and/or the stiffening member 80. For example, the stiffening member 80 may be subjected to a cold-forming process imparting a preformed curvature to the stiffening member 80. The preformed curvature of the stiffening member 80 may provide the cutting element 40 with a predictable orientation, such as a "12 o'clock" position as known in the art. Additionally, the preformed curvature of the stiffening member 80 may provide the distal portion of the elongate shaft 18 with a more uniform bowed configuration, without kinking, when the cutting element 40 is actuated proximally during operation. FIG. 3A is a cross-sectional view of the distal section 14 of the sphincterotome 10 assuming a bowed or curved position, such as when the cutting element 40 is activated by pulling the cutting element 40 proximally through the manipulation of the handle 16. As shown in FIG. 3A, when the cutting element 40 is activated, the exposed portion 46 of the cutting element 40 may form a chord between two points (e.g., the first side port 70 and the second side port 72) along the curved distal region 20 of the elongate shaft 18.

In embodiments where the stiffening member 80 includes a shape memory material, such as a shape memory alloy or a shape memory polymer, the stiffening member 80 may be configured to have a first shape and a second shape. Shape memory materials are those materials which are characterized by their responsiveness to thermal stimulus in order to transform between a first shape and a second shape. For example, the first shape may be a straight configuration and the second shape may be a curved configuration. The stiffening member 80 formed of a shape memory material may be programmed to transition from a straight configuration to a curved configuration at a predetermined temperature, for example a temperature just below the body temperature of a patient. In some embodiments, the predetermined temperature may be in the range of 70° F. to about 98° F., or in the range of 80° F. to about 95° F., or in the range of about 90° F. to about 95° F. In other words, the stiffening member 80 may assume a first shape at temperatures below the predetermined temperature, and may assume a second shape at temperatures above the predetermined temperature. In embodiments wherein the predetermined temperature is chosen to be at or below the body temperature of a patient, the stiffening member 80 may assume a first, straight configuration external of the body of the patient, but may transition to a second, curved configuration upon reaching the predetermined temperature within the body of the patient. Alternatively, the change in shape may be actuated by infusion of a warm fluid. The stiffening member 80 may be positioned in the distal section 20 of the elongate shaft 18 such that the bending plane of the stiffening member 80 in the curved configuration provides the cutting element 40 with a predictable orientation, such as a "12 o'clock" position, during a medical procedure.

FIG. 4A is a cross-sectional view through the distal section 14 of the elongate shaft 18. As shown in FIG. 4A, the stiffening member 80 may have a circular cross-section. The cross-section of the stiffening member 80 may substantially fill the second lumen 36, or the cross-section of the stiffening member 80 may occupy any portion of the second lumen 36. In some embodiments, the cross-section of the stiffening member 80 may be substantially similar to the cross-section of the cutting element 40.

FIGS. 4B-4D illustrate alternative embodiments of the cross-section of the stiffening member 80. FIG. 4B illustrates the stiffening member 80 as having an oval cross-section, FIG. 4C illustrates the stiffening member 80 as having a flattened or rectangular cross-section, and FIG. 4D illustrates the stiffening member 80 as having a semi-circular cross-section. The cross-sections illustrated in FIGS. 4B-4D, resultant of their respective moments of inertia (i.e., second moment of area) at the centroid of the cross-section, may provide the stiffening member 80 with a preferred bending plane, thus providing the cutting element 40 with a predictable orientation, such as a "12 o'clock" position, during operation.

In some embodiments, such as the illustrative embodiment of FIG. 3, the second lumen 36 terminates proximal of the distal end 22 of the elongate shaft 18. In such embodiments, at an intermediate stage of manufacture, the second lumen 36 may extend to the distal end 22 of the elongate shaft 18. The cross-section of the lumen may be made to complement the cross-section of the stiffening member. Therefore, the stiffening member 80 may be positioned within the second lumen 36 from the distal end 22 of the elongate shaft 18. Subsequently, the distal end 22 of the elongate shaft 18 may be subjected to a process wherein the extreme distal portion of the second lumen 36 is collapsed, filled, or otherwise occluded. For example, the distal end 22 of the elongate shaft 18 may be heated forming a molded distal tip 25, such that the extreme distal portion of the second lumen 36 is collapsed or closed off. Alternatively, the extreme distal portion of the second lumen 36 may be filled with a polymeric material, an adhesive, or other suitable material such that the extreme distal portion of the second lumen 36 is occluded.

Figure 5:
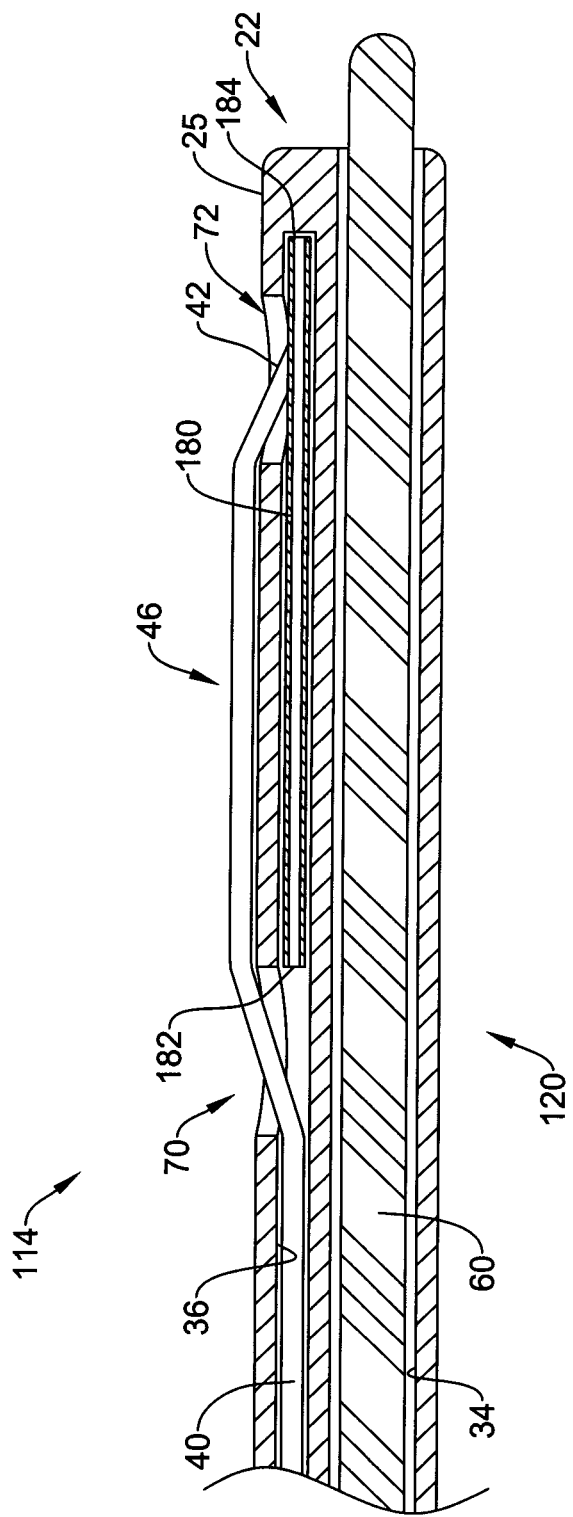
FIG. 5 is an alternative view of a distal section of an exemplary sphincterotome.

An alternative embodiment of a distal section 114 of the sphincterotome 10 is shown in FIG. 5. The distal section 114 illustrated in FIG. 5 is similar to the distal section 14 illustrated in FIG. 3, with the exception of certain aspects concerning the stiffening member 180. Thus, for the sake of repetitiveness, similarities of the distal section 114 with those of the distal section 14 will not be repeated.

The stiffening member 180, as shown in FIG. 5, may be a tubular member having a proximal end 182 and a distal end 184. The proximal end 182 may be positioned proximate the first side port 70 and the distal end 184 may be positioned proximate the second side port 72. In some embodiments, the stiffening member 180 may be disposed in a majority of the length of the segment of the second lumen 36 vacant of the cutting element 40. In other embodiments, the stiffening member 180 may be disposed in a substantial portion of the length of the segment of the second lumen 36 vacant of the cutting element 40. The tubular member may provide the stiffening member 180 with stiffening characteristics while retaining a passageway therethrough. The distal end 42 of the cutting element 40 may be secured to the stiffening member 180 proximate the second side port 72. Other aspects of the stiffening member 180 may be similar to those discussed above regarding the stiffening member 80. Therefore, for the sake of repetitiveness, notable similarities will not be repeated. For example, the stiffening member 180 may be subjected to a cold-forming process, may be formed of a shape memory material, or may have a cross-section providing the stiffening member 180 with a preferred bending plane, thus providing the cutting element 40 with a predictable orientation, such as a "12 o'clock" position, during operation.

Figure 6:
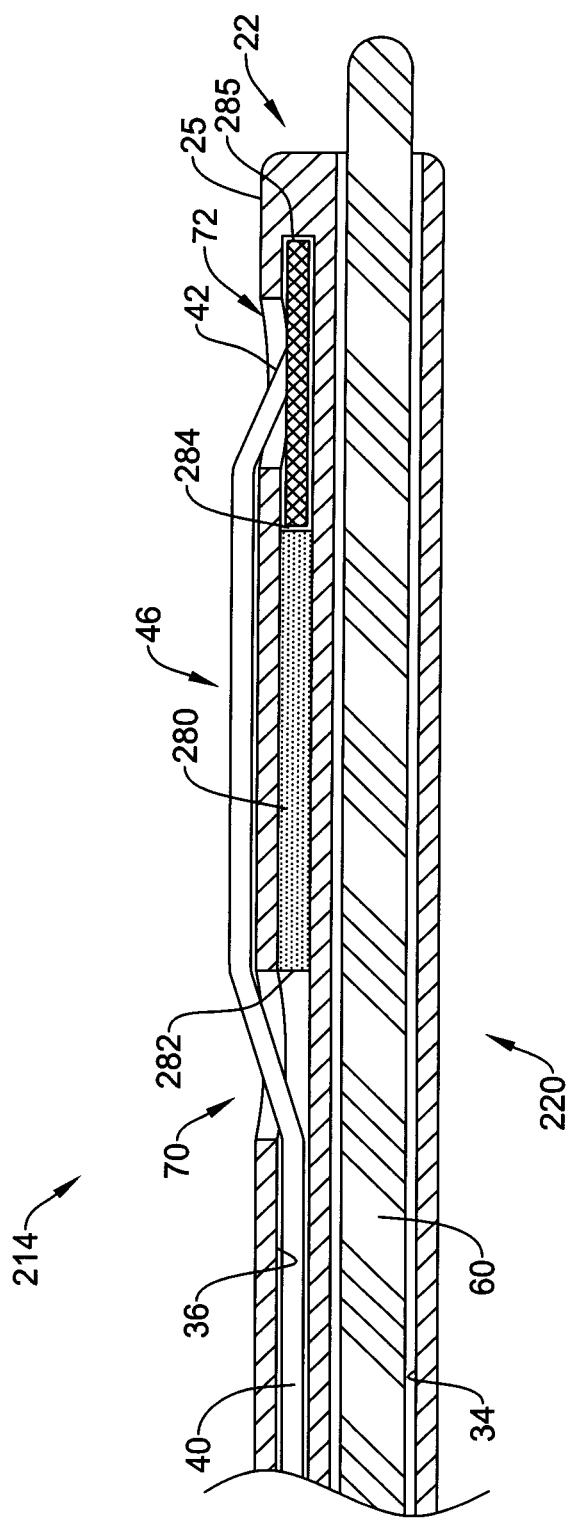
FIG. 6 is an alternative view of a distal section of an exemplary sphincterotome.

An alternative embodiment of a distal section 214 of the sphincterotome 10 is shown in FIG. 6. The distal section 214 illustrated in FIG. 6 is similar to the distal section 14 illustrated in FIG. 3, with the exception of certain aspects concerning the stiffening member 280 and the inclusion of an anchoring member 285. Thus, for the sake of repetitiveness, similarities of the distal section 214 with those of the distal section 14 will not be repeated.

The stiffening member 280, as shown in FIG. 6, may be a filler of material, such as a polymeric filler or an adhesive filler, having a proximal end 282 and a distal end 284. The proximal end 282 may be proximate the first side port 70 and the distal end 284 may be proximate the second side port 72. In some embodiments, the stiffening member 280 may be disposed in a majority of the length of the segment of the second lumen 36 vacant of the cutting element 40. In other embodiments, the stiffening member 280 may be disposed in a substantial portion of the length of the segment of the second lumen 36 vacant of the cutting element 40. Other aspects of the stiffening member 280 may be similar to those discussed above regarding the stiffening member 80. Therefore, for the sake of repetitiveness, notable similarities will not be repeated. For example, the stiffening member 280 may be formed of a shape memory material or may have a cross-section providing the stiffening member 280 with a preferred bending plane, thus providing the cutting element 40 with a predictable orientation, such as a "12 o'clock" position, during operation.

An anchoring member 285 may also be positioned in a portion of the second lumen 36 proximate the second side port 72. As shown in FIG. 6, the anchoring member 285 may be positioned distal of the stiffening member 280, for example abutting the distal end 284 of the stiffening member 280. In some embodiments, the anchoring member 285 may be secured to the stiffening member 280. However, in other embodiments, the anchoring member 285 may be unsecured to the stiffening member 280. The anchoring member 285 may be formed of any suitable material, such as a metallic material or a polymeric material, including but not necessarily limited to those materials listed herein. The distal end 42 of the cutting element 40 may be secured to the anchoring member 285 proximate the second side port 72.

Figure 7:
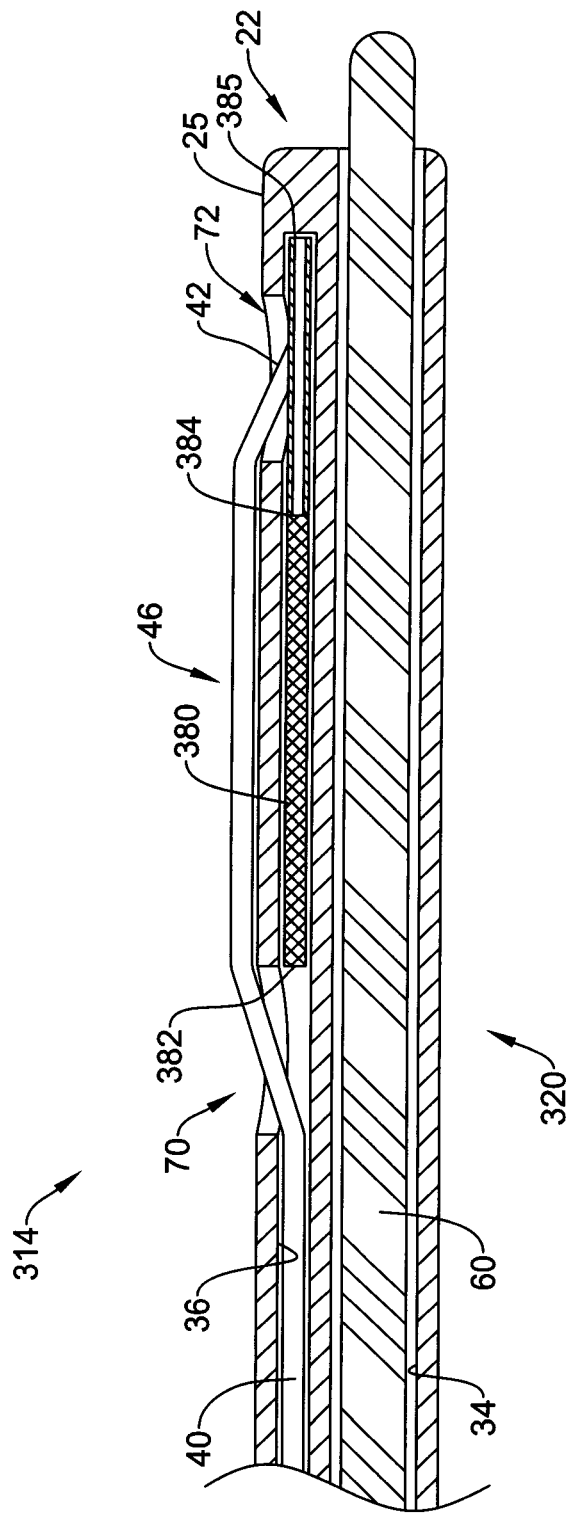
FIG. 7 is an alternative view of a distal section of an exemplary sphincterotome.

An alternative embodiment of a distal section 314 of the sphincterotome 10 is shown in FIG. 7. The distal section 314 illustrated in FIG. 7 is similar to the distal section 14 illustrated in FIG. 3, with the exception of certain aspects concerning the stiffening member 380 and the inclusion of an anchoring member 385. Thus, for the sake of repetitiveness, similarities of the distal section 314 with those of the distal section 14 will not be repeated.

The stiffening member 380, as shown in FIG. 7, may be a solid member having a proximal end 382 and a distal end 384. The proximal end 382 may be positioned proximate the first side port 70 and the distal end 384 may be positioned proximate the second side port 72. In some embodiments, the stiffening member 380 may be disposed in a majority of the length of the segment of the second lumen 36 vacant of the cutting element 40. In other embodiments, the stiffening member 380 may be disposed in a substantial portion of the length of the segment of the second lumen 36 vacant of the cutting element 40. Other aspects of the stiffening member 380 may be similar to those discussed above regarding the stiffening member 80. Therefore, for the sake of repetitiveness, notable similarities will not be repeated. For example, the stiffening member 380 may be subjected to a cold-forming process, may be formed of a shape memory material, or may have a cross-section providing the stiffening member 380 with a preferred bending plane, thus providing the cutting element 40 with a predictable orientation, such as a "12 o'clock" position, during operation.

An anchoring member 385 may also be positioned in a portion of the second lumen 36 proximate the second side port 72. As shown in FIG. 7, the anchoring member 385 may be positioned distal of the stiffening member 380, for example abutting the distal end 384 of the stiffening member 380. In some embodiments, the anchoring member 385 may be secured to the stiffening member 380. However, in other embodiments, the anchoring member 385 may be unsecured to the stiffening member 380. The anchoring member 385 may be formed of any suitable material, such as a metallic material or a polymeric material, including but not necessarily limited to those materials listed herein. The distal end 42 of the cutting element 40 may be secured to the anchoring member 385 proximate the second side port 72.

Figure 8:
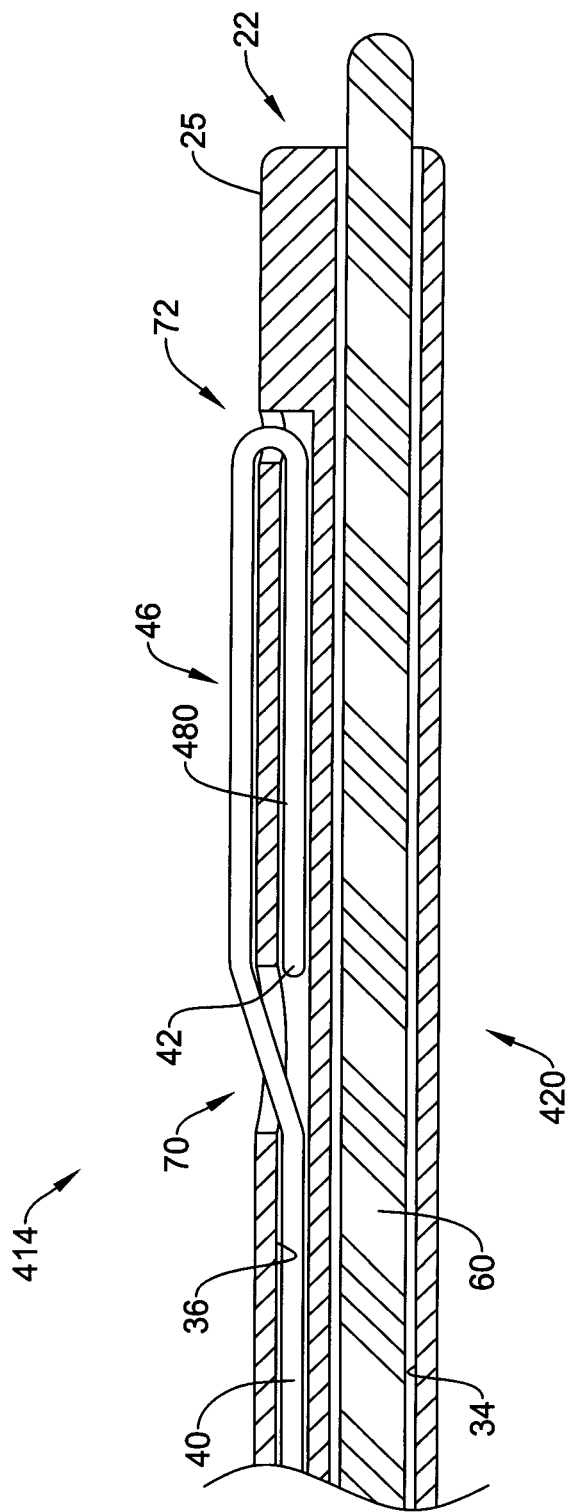
FIG. 8 is an alternative view of a distal section of an exemplary sphincterotome.

An alternative embodiment of a distal section 414 of the sphincterotome 10 is shown in FIG. 8. The distal section 414 illustrated in FIG. 8 is similar to the distal section 14 illustrated in FIG. 3, with the exception of certain aspects concerning the stiffening member 480. Thus, for the sake of repetitiveness, similarities of the distal section 414 with those of the distal section 14 will not be repeated.

The stiffening member 480, as shown in FIG. 8, may be an extension of the cutting element 40. For example, as shown in FIG. 8, a portion of the cutting element 40 may extend within the second lumen 36 through a portion of the elongate shaft 18 just proximal of the first side port 70. The cutting element 40 may then exit the second lumen 36 at the first side port 70 and continue distally exterior of the elongate shaft 18 and may reenter the elongate shaft 18 at the second side port 72. Therefore, the portion of the cutting element 40 extending between the first side port 70 and the second side port 72 external of the second lumen 36 may constitute an exposed portion 46 of the cutting element 40. The cutting element 40 may be doubled back upon itself such that after reentering the elongate shaft 18 through the second side port 72 a portion of the cutting element 40 extends from the second side port 72 proximally through the second lumen 36 toward the first side port 70. The portion of the cutting element 40 extending within the second lumen 36 between the second side port 72 and the first side port 70 may define the stiffening member 480. This portion of the stiffening member 80 can have any selected cross-sectional geometry as discussed above. In some embodiments, the end of the stiffening member 480 (i.e., the distal end 42 of the cutting element 40) may be positioned proximate the first side port 70. In some embodiments, the stiffening member 480 may be disposed in a majority of the length of the segment of the second lumen 36 between the second side port 72 and the first side port 70. In other embodiments, the stiffening member 480 may be disposed in a substantial portion of the length of the segment of the second lumen 36 between the second side port 72 and the first side port 70.

Other aspects of the stiffening member 480 may be similar to those discussed above regarding the stiffening member 80. Therefore, for the sake of repetitiveness, notable similarities will not be repeated. For example, the stiffening member 480 may be subjected to a cold-forming process, may be formed of a shape memory material, or may have a cross-section providing the stiffening member 480 with a preferred bending plane, thus providing the cutting element 40 with a predictable orientation, such as a "12 o'clock" position, during operation.

Figure 9:
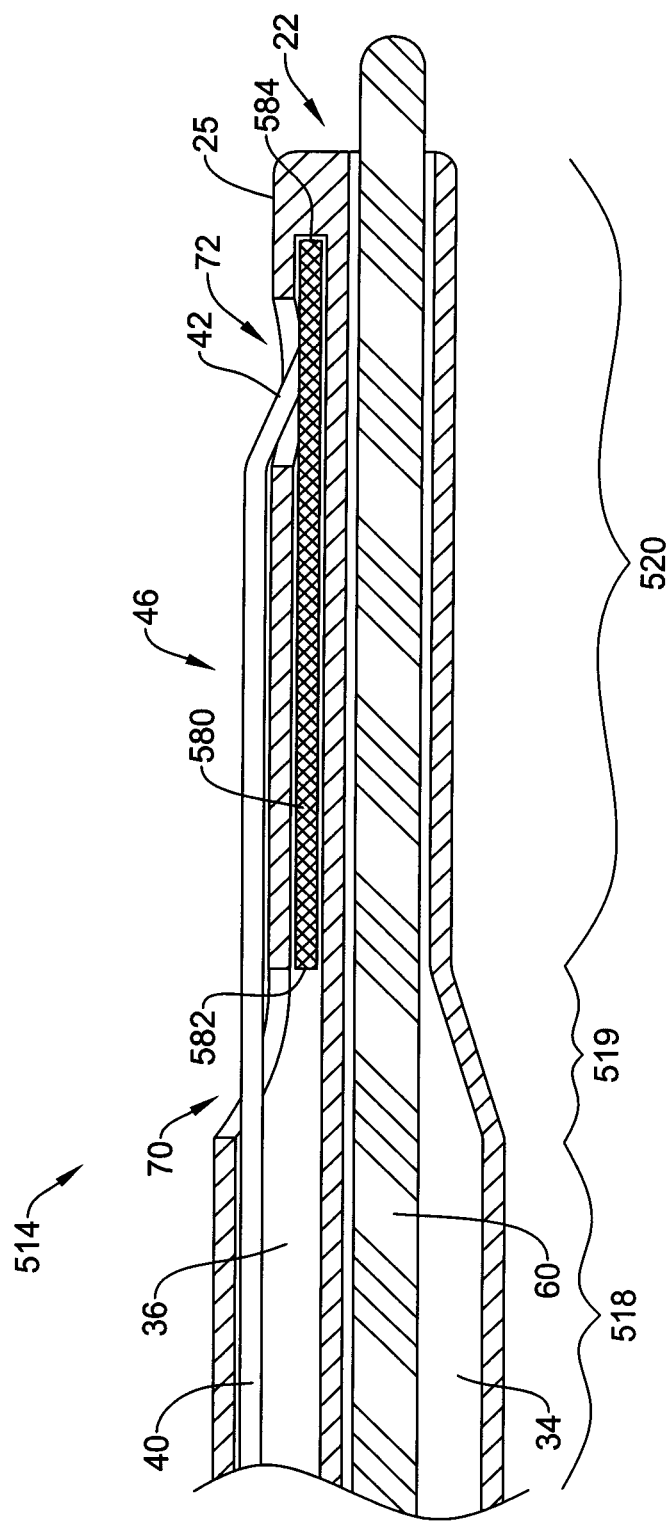
FIG. 9 is an alternative view of a distal section of an exemplary sphincterotome.

An alternative embodiment of a distal section 514 of the sphincterotome 10 is shown in FIG. 9. In many respects, the distal section 514 illustrated in FIG. 9 is similar to the distal section 14 illustrated in FIG. 3, with the exception that a distal portion 520 of the elongate shaft 18 includes a reduced diameter relative to a more proximal portion 518. Thus, for the sake of repetitiveness, similarities of the distal section 514 with those of the distal section 14 will not be repeated. It is noted that the terms "proximal" and "distal" in describing the portions of the elongate shaft 18 are intended to describe the relative spatial relationship between the proximal portion 518 and the distal portion 520.

As shown in FIG. 9, the proximal portion 518 of the elongate shaft 18 may have an outer diameter and the distal portion 520 of the elongate shaft 18 may have an outer diameter less than the outer diameter of the proximal portion 518. A tapered portion 519 may be positioned intermediate the proximal portion 518 and the distal portion 520 providing a transition between the proximal portion 518 and the distal portion 520. The reduced diameter or drawn-down distal portion 520 may provide the elongate shaft 18 with increased flexibility and/or maneuverability such that the sphincterotome 10 may be advanced through more tortuous and/or narrower pathways.

A portion of the cutting element 40 may extend within the second lumen 36 through a portion of the elongate shaft 18 just proximal of the first side port 70. The cutting element 40 may then exit the second lumen 36 at the first side port 70 and continue distally exterior of the elongate shaft 18 and may reenter the elongate shaft 18 at the second side port 72. Therefore, the portion of the cutting element 40 extending between the first side port 70 and the second side port 72 external of the second lumen 36 may constitute an exposed portion 46 of the cutting element 40.

A stiffening member 580 may be positioned within at least a portion of the length of the segment of the second lumen 36 vacant of the cutting element 40. The stiffening member 580 may have a proximal end 582 and a distal end 584. In some embodiments, the proximal end 582 of the stiffening member 580 may be proximate the first side port 70 and the distal end 584 of the stiffening member 580 may be proximate the second side port 72. In some embodiments, the stiffening member 580 may be disposed in a majority of the length of the segment of the second lumen 36 vacant of the cutting element 40. In other embodiments, the stiffening member 580 may be disposed in a substantial portion of the length of the segment of the second lumen 36 vacant of the cutting element 40.

Other aspects of the stiffening member 580 may be similar to those discussed above regarding the stiffening member 80. Therefore, for the sake of repetitiveness, notable similarities will not be repeated. For example, the stiffening member 580 may be subjected to a cold-forming process, may be formed of a shape memory material, or may have a cross-section providing the stiffening member 580 with a preferred bending plane, thus providing the cutting element 40 with a predictable orientation, such as a "12 o'clock" position, during operation.

Although an exemplary embodiment(s) of a sphincterotome has been disclosed, it is noted that alternate designs may be included. For example, the various lumens of a design may be made in fluid communication with one another to aid in fluid infusion.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. An electrosurgical cutting device comprising:
   an elongate shaft having a proximal end and a distal end, the elongate shaft including:
      a first lumen extending to the distal end of the elongate shaft;
      a second lumen terminating proximal of the distal end of the elongate shaft;
      a first side port extending through a sidewall of the elongate shaft at a location intermediate the proximal and distal ends of the elongate shaft, the first side port in communication with the second lumen; and
      a second side port extending through a sidewall of the elongate shaft at a location intermediate the first side port and the distal end of the elongate shaft, the second side port in communication with the second lumen;
   a cutting element extending through the second lumen proximal of the first side port and extending exterior of the elongate shaft between the first side port and the second side port; and
   a stiffening member positioned in the second lumen such that a proximal end of the stiffening member is located proximal of the second side port and a distal end of the stiffening member is located distal of the second side port, wherein the stiffening member has a solid cross-section which substantially fills the second lumen.

2. The electrosurgical cutting device of claim 1, wherein the stiffening member extends parallel with a portion of the cutting member extending exterior of the elongate shaft between the first side port and the second side port.

3. The electrosurgical cutting device of claim 1, wherein the cross-section of the stiffening member is substantially similar to a cross-section of the cutting element.

4. The electrosurgical cutting device of claim 1, wherein the stiffening member does not occupy any portion of the second lumen proximal of the first side port.

5. The electrosurgical cutting device of claim 1, wherein the second lumen has a length measured between the first side port and the second side port, and the stiffening member extends a majority of the length.

6. The electrosurgical cutting device of claim 1, wherein the proximal end of the stiffening member is positioned proximate the first side port.

7. The electrosurgical cutting device of claim 1, wherein the cutting element is secured to the stiffening member proximate the second side port.

8. The electrosurgical cutting device of claim 1, wherein the stiffening member is a portion of the cutting element extending proximally from the second side port.

9. The electrosurgical cutting device of claim 1, wherein the stiffening member is a polymeric filler.

10. A sphincterotome comprising:
    an elongate shaft having a proximal end and a distal end;
    a lumen extending through at least a portion of the elongate shaft;
    a first side port extending through a sidewall of the elongate shaft at a location intermediate the proximal and distal ends of the elongate shaft, the first side port in communication with the lumen;
    a second side port extending through a sidewall of the elongate shaft at a location intermediate the first side port and the distal end of the elongate shaft, the second side port in communication with the lumen;
    a cutting element extending through the lumen proximal of the first side port and extending exterior of the elongate shaft between the first side port and the second side port; and
    a stiffening member positioned in the lumen such that a proximal end of the stiffening member is located proximal of the second side port and a distal end of the stiffening member is located distal of the second side port;
    wherein the stiffening member does not occupy any portion of the lumen proximal of the first side port.

11. The sphincterotome of claim 10, wherein the lumen has a length measured between the first side port and the second side port, and the stiffening member extends a majority of the length.

12. The sphincterotome of claim 10, wherein the proximal end of the stiffening member is positioned proximate the first side port.

13. The sphincterotome of claim 10, wherein the cutting element is secured to the stiffening member proximate the second side port.

14. The sphincterotome of claim 10, wherein the stiffening member is a portion of the cutting element extending proximally from the second side port.

15. The sphincterotome of claim 10, wherein the stiffening member is a polymeric filler.

16. The sphincterotome of claim 10, wherein the stiffening member is a tubular member.

17. The sphincterotome of claim 10, wherein the stiffening member includes a shape memory material.

* * * * *